United States Patent [19]

Spector

[11] Patent Number: 5,030,214
[45] Date of Patent: Jul. 9, 1991

[54] OCULAR DELIVERY SYSTEM

[76] Inventor: Larry Spector, 255 Forest St., Hamden, Conn. 06518

[21] Appl. No.: 607,664

[22] Filed: Nov. 1, 1990

[51] Int. Cl.⁵ .................... A61H 33/04; A61M 35/00
[52] U.S. Cl. .................................. 604/301; 604/289; 604/294; 604/295; 604/297; 604/300
[58] Field of Search ............... 604/289, 294, 295, 297, 604/300, 301

[56] References Cited

U.S. PATENT DOCUMENTS

| | | | |
|---|---|---|---|
| 3,016,898 | 1/1962 | Erwin | 604/301 X |
| 4,052,985 | 10/1977 | Coleman et al. | 604/301 X |
| 4,131,115 | 12/1978 | Peng | 604/297 |
| 4,641,384 | 2/1987 | Landsberger et al. | 604/295 X |
| 4,792,334 | 12/1988 | Py | 604/295 X |
| 4,834,728 | 5/1989 | McKenna | 604/301 |

Primary Examiner—David J. Isabella
Assistant Examiner—Elizabeth M. Burke
Attorney, Agent, or Firm—Bachman & LaPointe

[57] ABSTRACT

An ocular delivery system for dispensing liquid eye treatment solution includes an eyecup to be placed over the eye to be treated, a system for forming a crescent shaped mist of treatment solution, and a system for collecting used solution without contaminating the source of fresh solution. The delivery system further includes an integral lid retractor for retracting the upper eyelid during treatment. The system is safe and easy to use as well as hygienic.

15 Claims, 1 Drawing Sheet

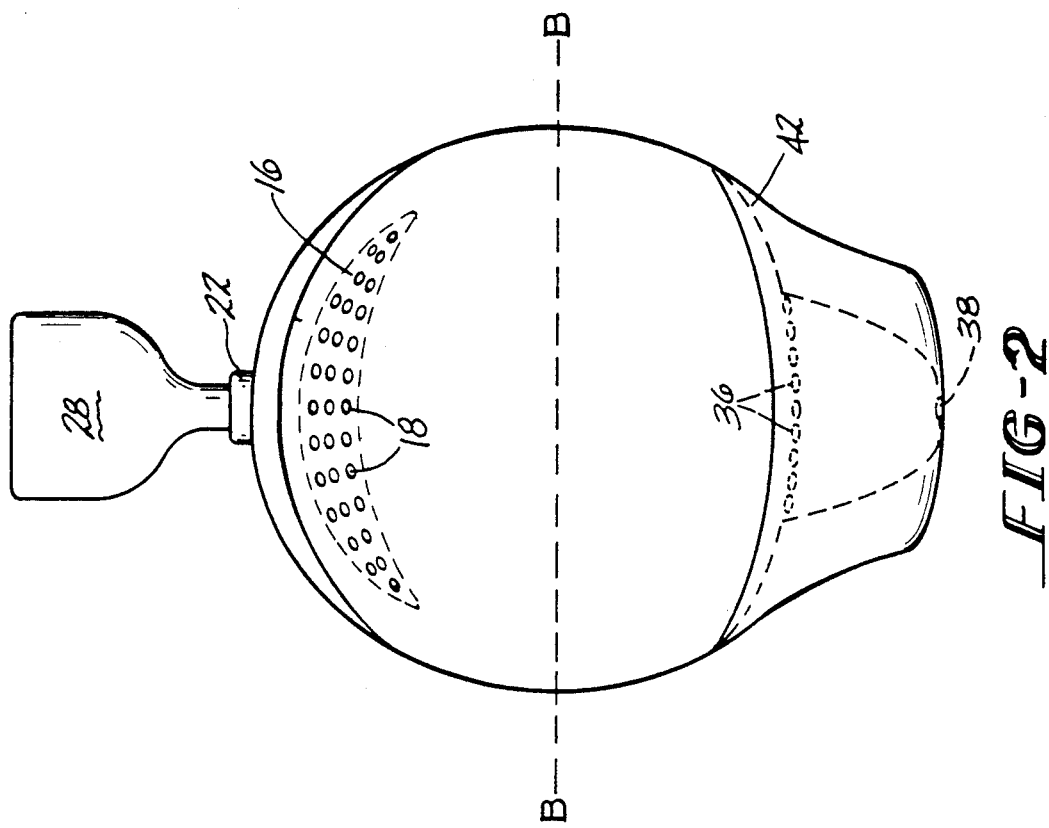
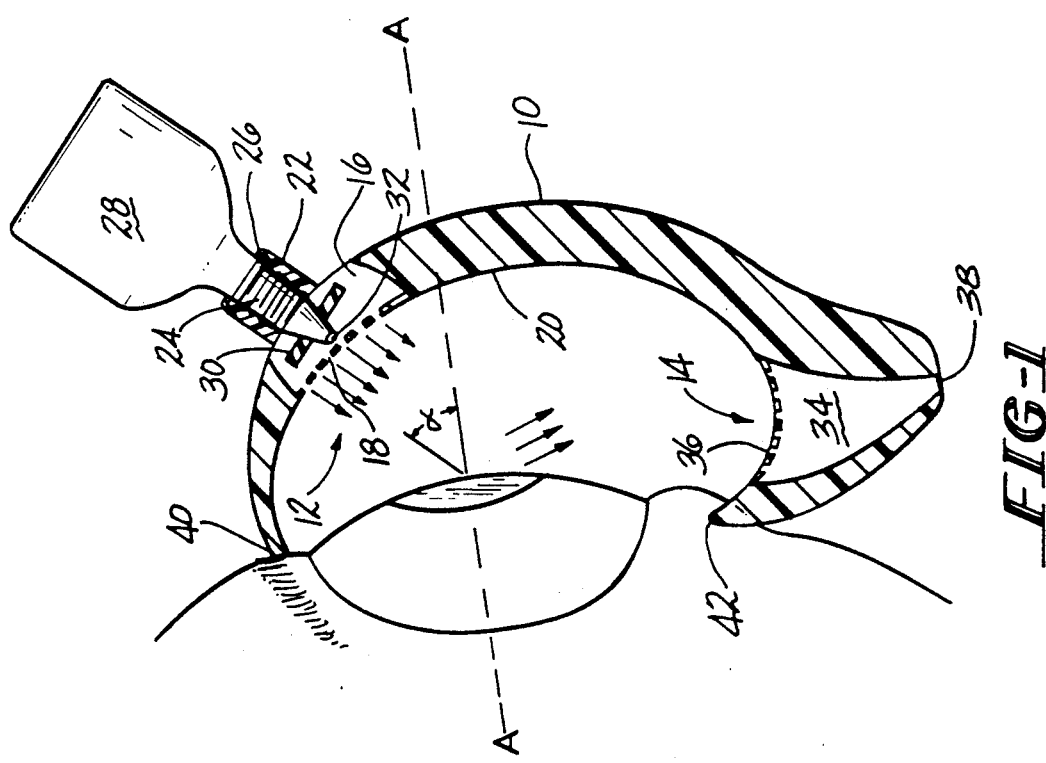

OCULAR DELIVERY SYSTEM

BACKGROUND OF THE INVENTION

The present invention relates to an ocular delivery system for dispensing medicinal or soothing liquids for treating or laving an eye.

Dispensers for supplying eye drops, eye medication and eye washing solutions are well known in the art. In their simplest form, dispensers have consisted of eyecups into which a liquid for treating or laving the eye is placed. Use of these eyecups typically requires the user to tilt his/her rearward which often results in liquid flowing down the user's face.

Some dispensers feature the eye cup directly secured to a container of the eye washing solution. U.S. Pat. No. 1,692,143 to Strunz, for example, illustrates the combination of a compressible rubber ball containing the liquid to be dispensed, an eye cup joined to the rubber ball, and a rose having a plurality of holes for creating jets of the liquid. In this dispenser, a space between the outer wall of the rose and the inner wall of the eye cup is used to collect liquid dropping back from the eye.

U.S. Pat. No. 2,231,112 to Conner illustrates an eyecup having a base member with a threaded portion for engaging the threaded neck of a bottle containing an eye washing solution. U.S. Pat. No. 4,834,728 to McKenna illustrates a similar type of dispensing apparatus.

U.S. Pat. No. 4,111,200 to Sharra et al. illustrates a dispenser for dispensing an exact number of drops into the center of an eye. The dispenser comprises an eyecup which is snapped over the cap of a bottle containing the eye drops.

U.S. Pat. No. 2,669,232 to Borowick illustrates yet another type of dispenser which has a base portion adapted to receive an eye lotion or liquid and an eyecup surmounting the base portion. The eyecup is connected to the base portion by means of a neck portion through which a valved passageway extends. By manipulation of the device, either prior to or during its application to the eye, the lotion or solution is caused to pass through the passageway from the container to the eyecup.

U.S. Pat. No. 3,888,251 to Harrison illustrates still another type of dispensing device. This device includes a container for holding the liquid to be dispensed, an eyecup, and a deformable squeeze bulb affixed to the eyecup. The bulb communicates with the fluid in the container via a tube. By squeezing the bulb, fluid is drawn into it from the container. The eyecup and bulb are then removed from the container and positioned over the user's eye. Squeezing the bulb a second time causes the fluid to flow out of the bulb into the user's eye.

U.S. Pat. No. 4,131,115 to Peng illustrates an eyewashing device having a manually operated eyelid turning member. The device further includes a drain tube for removing eye washing solution from the eyecup.

All of these dispensers suffer from the disadvantages of requiring the user to tilt his head, something which can be difficult for elderly users. Most of the dispensers suffer the disadvantage of allowing eye secretions and/or debris to mix with the eye solution and re-enter the eye. Thus, the eye solution can become contaminated and infection could result. Still other disadvantages of these dispensers including the absence of means to prevent solution from dripping down a person's face into a person's mouth and/or onto a person's clothing.

SUMMARY OF THE INVENTION

Accordingly, it is an object of the present invention to provide an ocular delivery system which avoids the aforenoted disadvantages of the prior art dispensers.

It is a further object of the present invention to provide an ocular delivery system which is safe and easy to use.

It is still a further object of the present invention to provide an ocular delivery system which is hygienic and avoids contamination of the eye solution.

It is yet a further object of the present invention to provide an ocular delivery system which can be used with a wide variety of eye washing solutions, eye medications, and eye drops.

These and other objects and advantages will become more clearer from the following description and drawings in which like reference numerals depict like elements.

An ocular delivery system in accordance with the present invention is characterized by an eyecup portion, means for joining the eyecup portion to a compressible container holding the liquid to be applied to the eye, and means for dispensing the liquid while the patient's or user's head is in a substantially erect position. The dispersing means comprises a crescent shaped mist system located in the upper half of the eyecup for allowing the liquid to be introduced into the eye at an angle of between about 45° to about 60° relative to a plane passing through the center of the eye being treated and parallel to an equatorial plane of the eyecup. It has been found that there are numerous advantages for introducing the liquid treatment solution into the eye being treated in this manner. The advantages include: (1) being able to keep the patient's or users head in a natural, straight position; (2) better application of the liquid to the upper sclera and cornea; (3) the ability to let gravity wash debris down toward the tear duct and toward a collection basin; (4) the ability to keep debris and excess solution away from the eyelid margin; and (5) the ability to prevent used liquid and eye secretions from mixing with the primary source of the liquid.

The ocular delivery system of the present invention is further characterized by a liquid collection basin and a lid retractor built into the eyecup. The collection basin allows used liquid to be gathered so as to prevent contamination of the fresh liquid and so as to prevent it from dripping down a patient's or user's face. The integral lid retractor allows the liquid to be applied against the anterior surface of the eye below the upper lid margin.

Still other features of the present invention will become more apparent from the following description and drawings.

BRIEF DESCRIPTION OF THE DRAWINGS

FIG. 1 is a sectional view of the ocular delivery system of the present invention; and FIG. 2 is a front view of the ocular delivery system of FIG. 1.

DETAILED DESCRIPTION

The ocular delivery system of the present invention comprises an eyecup 10 formed from either a plastic material or hard rubber material which can be sterilized in hot water. If formed from a plastic material, the eyecup 10 could be formed from either a clear or opaque plastic material. The eyecup 10 preferably has a concave interior shape or configuration.

The eyecup 10 has integrally formed means 12 for dispensing an eye treatment liquid solution while a patient's or user's head is in a substantially erect position and an integrally formed collection basin 14 for collecting used eye solution. For reasons which will be explained more fully hereinafter, the dispensing means is located in the upper half of the eyecup, i.e., that portion above the equatorial plane B—B, and the collection basin is located in the lower half of the eyecup.

The dispensing means 12 comprises a hollow chamber 16 formed in the eyecup and a plurality of holes 18 formed in the interior surface 20 of the eyecup for communication with the chamber 16. As shown in FIG. 1, the chamber 16 and the holes 18 are arranged to form a spray pattern at an angle of from about 45° to about 60° with respect to a substantially horizontal plane A—A containing the center of the eye being treated and extending parallel to the equatorial plane B—B of eyecup. It has been found that delivering a liquid to an eye at this angle provides several advantages. These include the ability to maintain the patient's or user's head in a naturally straight position during use. Not having to tilt one's head during use is particularly beneficial to elderly users or patients. It also facilitates keeping the eyelids open, keeping the eye looking straight ahead during treatment, and obtaining a better application of the liquid to the upper sclera and cornea. Still further, gravity will wash any debris toward the tear duct and the collection basin 14. As a result, used liquid and any eye secretions cannot mix with the primary liquid being applied and/or re-enter the eye. This prevents contamination of the primary eye solution as well as substantially reduce the possibility of infection.

As shown in FIG. 2, the holes 18, as well as the underlying chamber 16, a have a crescent shape configuration. It has been found that forming a crescent shaped mist using this arrangement naturally pushes any debris toward the middle of the eye and down. As a result, it keep debris and excess liquid away from the eyelid margin. Still further, the used liquid and any eye secretions are pushed toward the collection basin 14.

The dispensing means further includes an integrally formed receptacle 22 for receiving the neck portion 24 of a compressible bottle 28 containing the treatment solution. The receptacle 22 may be internally threaded if desired to engage a set of threads on the neck portion 24. Alternatively, the receptacle 22 may have an inwardly directed portion 26 for snapping the eyecup onto the bottle 28.

As shown in FIG. 1, a rubber O-ring 30 is positioned within the chamber 16. The O-ring has a central opening for receiving the apertured tip 32 of the bottle 28. The O-ring allows a snug fit between the eyecup and the bottle while preventing splash back. The O-ring may be seated in the chamber 16 in any desired manner. For example, the chamber 16 may be fabricated around the O-ring 30 during manufacture of the eyecup.

The collection basin 14 is also formed by a hollow chamber 34 having a plurality of holes 36 in the interior surface 20. The holes 36 may be arranged in any desired pattern, e.g., crescent shaped. Similarly, the chamber 34 may have any desired shape. The collection basin 14 further has an outlet opening 38 which allows used liquid and debris to be gathered in a separate container. The collection basin helps eliminate the problem of used solution leaving the area enclosed by the eyecup and dripping down a patient's or a user's face and into his/her mouth.

The eyecup 10 further has a relatively blunt edge 40 which acts as a lid retractor to passively hold the patient's or user's upper eyelid against the upper brow. This feature is desirable from the standpoint of allowing the jets or mist of solution to contact the anterior surface of the eye just below the upper lid margin.

The lower portion of the eyecup 10 further has an upturned edge 42 which presses against the patient's or user's check. This upturned edge helps to prevent used liquid from dripping down the patient's or user's cheek and helps to direct the used liquid into the collection basin.

To use the ocular delivery system of the present invention, a user first joins the compressible bottle 28 containing the eye solution to the eyecup 10 either by threading the bottle into the receptacle 22 or by snapping the receptacle 22 onto the bottle. The eyecup with the attached bottle is then placed over the eye to be treated and pressed against a patient's or user's face so that the upper eyelid is retracted and the upturned edge 42 presses against the patient's or user's cheek. The bottle is then squeezed so as to expel the treatment solution under pressure into the dispensing chamber 16 and through the mist creating holes 18. After the sprayed liquid contacts the eye, excess liquid and any debris or eye secretions are propelled downwardly by gravity toward the collection basin 14. The excess liquid, debris and/or eye secretions enter the collection basin and are drained out of the eyecup 10 via outlet 38 into a cup or container (not shown).

As can be seen from the foregoing discussion, a hygienic ocular delivery system has been provided which is safe and easy to use by both physicians and individuals. The system prevents the accumulation of mucus and debris from the lid margin which reduces the chance of the meibomian and lacrimal ducts from becoming clogged, thus reducing the chance of hordeolums and styes. The system also prevents any contamination of the fresh eye solution by used solution, debris, and eye secretions.

The ocular delivery system of the present invention may be used to apply any liquid eye solutions including, but not limited to, laving solutions, medicaments, contact lens solutions, glaucoma Px's, eye drops and the like. The ocular delivery system of the present invention reduces the possibility of spreading infections.

It is apparent that there has been provided in accordance with this invention an ocular delivery system which fully satisfies the objects, means and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. An ocular delivery system for spraying a solution onto an eye which comprises:
   an eyecup having an equatorial plane; and
   means for dispensing said solution while the head of a person to whom the solution is being applied is in a substantially erect position, said dispensing means comprising a plurality of holes arranged in a crescent shaped configured in an interior surface of said eyecup for introducing said solution into said eye at an angle between about 45° to about 60° with respect to a plane passing through the center eye of said eye which is substantially parallel to said equatorial plane.

2. The ocular delivery system of claim 1 wherein said holes are located in the upper half of said eyecup.

3. The ocular delivery system of claim 1 wherein said eyecup is formed from a hard plastic material.

4. The ocular delivery system of claim 1 wherein said eyecup is formed from hard rubber.

5. The ocular delivery system of claim 1 wherein said eyecup has a concavely shaped interior surface.

6. The ocular delivery system of claim 1 wherein said dispensing means further comprises means for mounting a container with said eye solution to said eyecup.

7. The ocular delivery system of claim 6 wherein said mounting means comprises an integrally formed portion for receiving a neck of said container and snapping it into place.

8. The ocular delivery system of claim 6 wherein said mounting means comprises an integrally formed receptacle portion having internal threads for engaging a threaded portion of said container.

9. The ocular delivery system of claim 6 wherein said dispensing means further comprises:
   a hollow chamber in said eyecup;
   said hollow chamber having an aperture for receiving a tip portion of said container; and
   said plurality of holes communicating with said hollow chamber.

10. The ocular delivery system of claim 9 further comprising:
    an O-ring positioned within said hollow chamber for properly positioning said container and preventing splash back of said solution.

11. An ocular delivery system for spraying a solution onto an eye which comprises:
    an eyecup having an equatorial plane;
    means for dispensing said solution while the head of a person to whom the solution is being applied is in a substantially erect position, said dispensing means comprising means for introducing said solution into said eye at an angle between about 45° to about 60° with respect to a plane passing through the center of said eye which is substantially parallel to said equatorial plane;
    means for collecting used solution, eye debris and eye secretions; and
    said collecting means being located within a lower half of said eyecup.

12. The ocular delivery system of claim 11 wherein said collecting means comprises:
    a hollow chamber within a lower portion of said eyecup;
    a plurality of holes communicating with said chamber for removing said used solution, eye debris and eye secretions from said eyecup; and
    an outlet opening communicating with said chamber.

13. The ocular delivery system of claim 12 wherein said collecting means further comprises an upturned edge portion for directing said used solution, eye debris and eye secretions toward said holes and said chamber.

14. An ocular delivery system for spraying a solution onto an eye which comprises:
    an eyecup having an equatorial plane;
    means for dispensing said solution while the head of a person to whom the solution is being applied is in a substantially erect position, said dispensing means comprising means for introducing said solution into said eye at an angle between about 45° to about 60° with respect to a plane passing through the center of said eye which is substantially parallel to said equatorial plane; and
    said eyecup having an integrally formed blunt edge which acts as an upper eyelid retractor.

15. An ocular delivery system for applying a liquid to a person's eye while the head of said person is in a substantially erect position which comprises:
    an eyecup having an upper half and a lower half;
    means for applying said liquid to said eye positioned solely in said upper half; and
    means for collecting used solution and removing it from said eyecup located in said lower half.

* * * * *